United States Patent [19]

Fleckenstein et al.

[11] Patent Number: 5,124,491

[45] Date of Patent: * Jun. 23, 1992

[54] PROCESS FOR THE HYDROGENATION OF FATTY ACID METHYL ESTERS

[75] Inventors: Theo Fleckenstein, Hilden; Joachim Pohl, Duesseldorf; Franz J. Carduck, Haan, all of Fed. Rep. of Germany

[73] Assignee: Henkel Kommanditgesellschaft auf Aktien, Duesseldorf, Fed. Rep. of Germany

[*] Notice: The portion of the term of this patent subsequent to Aug. 27, 2008 has been disclaimed.

[21] Appl. No.: 504,735

[22] Filed: Apr. 3, 1990

Related U.S. Application Data

[63] Continuation of Ser. No. 222,454, Jul. 22, 1988, abandoned.

[30] Foreign Application Priority Data

Jul. 22, 1987 [DE] Fed. Rep. of Germany ....... 3724254

[51] Int. Cl.$^5$ ................. C07C 29/149; C07C 31/125; C07C 31/04
[52] U.S. Cl. ..................................... 568/885; 502/241
[58] Field of Search .......................................... 568/885

[56] References Cited

U.S. PATENT DOCUMENTS

| | | | |
|---|---|---|---|
| 2,080,419 | 5/1937 | Green | 568/885 |
| 2,091,800 | 8/1937 | Adkin et al. | 568/885 |
| 2,094,127 | 9/1937 | Lazier | 568/885 |
| 2,109,844 | 3/1938 | Lazier | 568/885 |
| 3,173,959 | 3/1965 | Rittmeister | 260/638 |
| 3,180,898 | 4/1965 | Eisenlohr et al. | 568/885 |
| 3,193,586 | 7/1965 | Rittmeister | 260/638 |
| 4,113,662 | 9/1978 | Wall | 252/473 |
| 4,199,479 | 4/1980 | Wilkes | 252/457 |
| 4,433,175 | 2/1984 | Kaufhold | 568/885 |
| 4,482,766 | 11/1984 | Stönner | 568/885 |
| 4,611,085 | 9/1986 | Kitson | 568/885 |
| 4,652,685 | 3/1987 | Cawse et al. | 568/885 |

FOREIGN PATENT DOCUMENTS

| | | |
|---|---|---|
| 2613226 | 12/1978 | Fed. Rep. of Germany . |
| 3425758 | 1/1985 | Fed. Rep. of Germany . |
| 2513377 | 8/1985 | Fed. Rep. of Germany . |
| 124510 | 3/1971 | India . |

OTHER PUBLICATIONS

Ullmanns Encyklopaedie der technischen Chemie, 4th Edition, vol. 11, pp. 427–445.

Primary Examiner—J. E. Evans
Attorney, Agent, or Firm—Ernest G. Szoke; Wayne C. Jaeschke; John E. Drach

[57] ABSTRACT

In the catalytic hydrogenation of fatty acid methyl esters, the fatty acid methyl esters are continuously reacted with hydrogen under pressures of from 20 to 100 bar and at temperatures of from 160° to 270° C. with molar ratios of hydrogen to fatty acid methyl ester substrate of from 10:1 to 500:1. The reaction is carried out over catalysts which contain from 30 to 40% by weight copper, from 23 to 30% by weight chromium, from 1 to 10% by weight manganese, from 1 to 10% by weight silicon and from 1 to 7% by weight barium (% by weight, based in each case on oxidic catalyst mass) and, if desired, other transition metals in the form of their oxides. After calcination of the components, the catalyst is converted into shaped particulate and/or granulated elements with from 1 to 10% by weight, based on oxidic catalyst, of at least one binder in addition to 1 to 10% by weight graphite. The catalyst is activated with hydrogen or a hydrogen-containing gas mixture. This process enables production of fatty alcohols in high yield from pre-separated distillation cuts of fatty acid methyl esters at low pressures and very low hydrocarbon formation.

17 Claims, No Drawings

PROCESS FOR THE HYDROGENATION OF FATTY ACID METHYL ESTERS

This application is a continuation of application Ser. No. 07/222,454, filed Jul. 21, 1988, now abandoned.

BACKGROUND OF THE INVENTION

1. Field of the Invention

This invention relates to a new process for the catalytic hydrogenation of fatty acid methyl esters using particulate and/or granulated catalysts containing copper chromite under pressures in the range from 20 to 100 bar.

2. Description of Related Art

Fatty alcohols, i.e., predominantly linear, monofunctional alcohols having chain lengths of 8 and more carbon atoms, and their production are described in detail in the literature, for example, in Ullmanns Encyklopaedie der technischen Chemie, 4th Edition, Vol. 11, pages 427 to 445. A preferred starting material for their production are the fatty acids and fatty acid mixtures occurring in natural fats and/or oils which may be converted into fatty alcohols of corresponding chain length by catalytic hydrogenation. Through the use of the fatty acids to be reduced in the form of their methyl esters, the catalysts in particular are protected against aggressive attack by the free carboxyl group, so that industrial processes can be operated for sufficiently long periods with satisfactory volume-time yields. Today, therefore, the predominant quantity of native fatty alcohols is produced from fatty acid methyl esters by the gas-phase hydrogenation process in which the distilled methyl esters are passed in the vapor phase, together with a large excess of hydrogen, over a fixed bed of copper-containing mixed oxide catalysts, such as, for example, copper chromite spinel catalysts, at temperatures above 200° C. and under pressures of from about 250 to 300 bar.

The copper-mixed oxide catalysts obtained by coprecipitation via the wet route are used as particulate catalysts or extrudates and, before use, are generally reduced in the plant or installation.

According to the relevant patent literature, fatty acid esters, more especially fatty acid methyl esters, and free fatty acids are therefore simultaneously used as starting materials for the hydrogenation reaction to saturated and/or unsaturated fatty alcohols, for example, as described in German Patent Publications DE-PSS 965 236, 10 05 497, 25 13 377 and 26 13 226. U.S. Pat. Nos. 4,113,662, 4,482,766, and 4,199,479 as well as Indian Patent 124510 also describe pertinent process features. As far as industrial application is concerned, the proposals mentioned have to be evaluated entirely differently according to whether the fatty acid esters or the free fatty acids are used as starting material for the hydrogenation.

German Patent Publication DE-OS 34 25 758 describes a process for the production of alcohols, more particularly either furfuryl alcohol by hydrogenation of furfural or fatty alcohol by hydrogenation of fatty acids containing a corresponding number of carbon atoms or esters thereof under a pressure in the range from 20 to 100 bar. The process is carried out at a temperature in the range from 150° to 300° C. and in the presence of a catalyst containing a mixture of copper and chromium on the one hand and copper on a support on the other hand. Under the described conditions, reduction of the fatty alcohols to the corresponding hydrocarbons is also observed in practice thereby jeopardizing the economy of the process through a reduction in yield. Another disadvantage is the fact that the catalysts used in the prior processes show inadequate mechanical strength. The solid catalyst is extremely difficult to separate from the reaction products and this causes losses of active catalyst through washing away of catalyst material.

DESCRIPTION OF THE INVENTION

Other than in the operating examples, or where otherwise indicated, all numbers expressing quantities of ingredients or reaction conditions used herein are to be understood as modified in all instances by the term "about".

It has now surprisingly been found that it is possible with certain highly active long-life catalysts and under comparatively moderate reaction conditions, particularly under relatively low reaction pressures, to control the hydrogenation of fatty acid methyl esters to fatty alcohols in such a way that very few, if any, hydrocarbons are formed as secondary products.

An object of the present invention is to provide a process for the catalytic hydrogenation of fatty acid methyl esters using particulate and/or granulated catalysts containing copper chromite, by which fatty acid methyl esters can be reacted to fatty alcohols in high yields under relatively low pressures. The heterogeneous transition-metal catalyst used for the reaction leads to the required products with high activity and selectivity without secondary reactions, such as the formation of hydrocarbons, significantly contributing towards a reduction in the product yield. Together with the establishment of moderate reaction conditions, this improves the economy of the process in relation to the prior art.

The formation of hydrocarbons is minimal because, when the hydrogenation products are worked up by distillation, the boiling ranges of the hydrocarbon products overlap those of the short-chain fatty alcohols.

The present invention relates to a process for the catalytic hydrogenation of fatty acid methyl esters at elevated reaction temperatures using particulate and/or granulated catalysts containing copper chromite as principal constituent, which comprises continuously reacting with hydrogen fatty acid methyl esters under pressures of 20 to 100 bar and at temperatures of from 160° to 270° C. with molar ratios of hydrogen to fatty acid methyl ester substrate of from 10:1 to 500:1. The reaction is carried out over catalysts which contain from 30 to 40% by weight copper, from 23 to 30% by weight chromium, from 1 to 10% by weight manganese and from 1 to 7% by weight barium (% by weight, based in each case on oxidic catalyst mass) and, if desired, other transition metals in the form of their oxides and which, after calcination of the components forming the catalyst mass, have been converted into shaped particulate and/or coarse-grained elements with from 1 to 10% by weight, based on oxidic catalyst, of at least one binder in addition to 1 to 10% by weight graphite and activated with hydrogen or a hydrogen-containing gas mixture.

Fatty acid methyl esters suitable for catalytic hydrogenation by the process according to the invention may be of native or synthetic origin. Suitable starting materials for the hydrogenation process according to this invention are the fats, train oils or oils emanating from animal or vegetable sources in which mono- or polyunsaturated fatty acids are esterified with glycerol, the fatty acid residues optionally having the same or different degrees of saturation and alkyl chain lengths. The fatty acid methyl esters may be obtained by transesterification in known manner from the above-mentioned fats, train oils and oils. Methyl ester mixtures such as these are separated up by distillation processes into relatively short-chain and relatively long-chain fatty acid residues and subsequently hydrogenated.

In the process of this invention, the catalytic hydrogenation of the fatty acid methyl esters is carried out in the presence of a catalyst which contains (based on the oxidic catalyst mass) from 30 to 40% by weight copper, from 23 to 30% by weight chromium, from 1 to 10% by weight manganese, from 1 to 7% by weight barium, and, optionally, other transition metals. The metals mentioned are present in the form of their oxides after production of the catalyst masses which is carried out by methods known in the prior art. Oxide formation takes place, as known from the prior art, during the so-called "calcination," i.e. by thermal decomposition of mineral salts of the particular metals.

In the process of this invention, a catalyst containing from 1 to 10% by weight $SiO_2$, based on the oxidic catalyst mass, is used for the hydrogenation of the fatty acid methyl esters.

In one preferred embodiment of the process of this invention, fatty acid methyl esters are continuously hydrogenated using a catalyst advantageously containing from 32 to 38% by weight copper, based on the oxidic catalyst mass. It is also advantageous to adjust the quantity of chromium in the catalyst to a range of from 26 to 29% by weight, the quantity of manganese to a range of from 1 to 10% by weight, the quantity of barium to a range of from 1.5 to 3% by weight and the quantity of silicon to a range of from 1.5 to 3% by weight, based in each case, on the oxidic catalyst mass before activation. In one particularly preferred embodiment, a catalyst containing 36% by weight copper, 29% by weight chromium, 2.5% by weight manganese, 1.7% by weight barium and 1.0% by weight silicon, based in each case on the oxidic catalyst mass before activation, and optionally other transition metals in the form of their oxides is used for the catalytic hydrogenation of fatty acid methyl esters. With the catalysts as described herein, it is possible to obtain considerable increases in activity, even under relatively low pressures. For this reason, the use of such catalysts in the process of this invention is regarded as particularly preferred.

In another preferred embodiment of the process of this invention, a catalyst containing other transition metals in the form of their oxides in addition to the above-mentioned quantities of copper, chromium, manganese, barium and silicon is used for the catalytic hydrogenation of fatty acid methyl esters. Thus, it is possible to use a catalyst containing from 1 to 5% by weight and, preferably, from 2 to 3% by weight each of zirconium and/or cerium in addition to the metals described above. In this connection, it is possible to add one of the transition metals mentioned in the form of its oxides or even several of the transition metals mentioned in the form of their oxides in admixture with one another to the catalysts in accordance with this invention. The use of additionally doped catalysts such as described in the process of this invention leads to a considerable increase in the activity and selectivity of the catalysts, particularly where hydrogenation is carried out in a trickling bed. In particular, the formation of hydrocarbons is suppressed by this process.

Catalysts employed in the process of this invention preferably contain from 1 to 10% by weight of graphite to improve the processibility of the granulates and/or extrudates. A quantity of 5% by weight of graphite is most preferably added to and thoroughly mixed with the calcined powder-form material before granulation.

According to the invention, an improvement in the process is obtained by bringing the catalyst containing the above-mentioned metals in the form of their oxides and graphite into granulate or extrudate form using from 1 to 10% by weight of one or more binders and preferably 10% by weight of one or more binders. Suitable binders are compounds known for this purpose from the prior art, of which either one or even several are used in the catalyst employed in accordance with the process of this invention. The use of one or more binders selected from polyvinyl acetate and methyl methacrylate has proved to be particularly effective. In contrast to numerous, non-free-flowing catalyst materials known from the prior art, it was possible to provide a catalyst in granulate or extrudate form for the process of this invention, of which the loosened, porous structure contributes significantly to increasing the activity and selectivity of the catalyst in the hydrogenation of the fatty acid methyl esters under relatively low pressures, particularly in a trickling bed. Polyvinyl acetate is preferably used as binder for the production of the catalyst granulates or extrudates. Commercially obtainable 40% by weight polyvinyl acetate suspensions, for example, are used for the production of the catalyst. After thorough mixing, polyvinyl acetate suspensions are added in small quantities to the calcined, powder-form catalyst materials and mixed therewith until agglomerate grains begin to build up. The agglomerate-containing powder is then compacted to small granulates, for example, in a perforated-roll granulator. These techniques are known from the prior art. The granulates are dried, again in known manner, to residual moisture contents of from 10 to 15%. The granulates resulting from this operation are sieved, grain fractions of a certain grain size being sieved out for the process of this invention. Catalyst grain fractions having a grain size of from 0.6 to 3 mm are advantageously used where the process of this invention is used for the catalytic hydrogenation of fatty acid methyl esters in a trickling bed.

The catalysts can be compressed into tablet form, for example, into 4×4 mm tablets. For hardening, the tablets are tempered in air for 6 h at a temperature of 200° to 280° C. The specific surface as determined by the BET method (Z. Anal. Chem. 288 (1968), 187–193) was 40±10 $m^2/g$.

The granulated catalysts suitable for use in the process of this invention for the hydrogenation of fatty acid methyl esters have a specific surface of 30 to 50 $m^2/g$. The described form of pregranulation leads to a special, loosened pore structure which increases the degree of pore utilization.

In the practice of the process of this invention for the hydrogenation of fatty acid methyl esters, it has been found to be of particular advantage to react the fatty acid methyl esters with hydrogen in the presence of a catalyst of which the granulates, extrudates or tablets have a diameter of from 1 to 6 mm and a length of from 1 to 6 mm. Such granulates or extrudates (tablets) show excellent activity and selectivity in the reaction of the fatty acid methyl esters with hydrogen to long-chain fatty alcohols and, in addition, readily can be separated from the reaction products. In addition, the useful lives obtainable with such catalysts are considerably better than the useful lives of the catalysts known from the prior art. In addition, prior catalysts have the disadvantage that, in some cases, they disintegrate during the reaction and as a result can be separated from the reaction products only with considerable difficulty.

Another factor significantly affecting the activity and selectivity of the catalysts used in accordance with the process of this invention is the pore volume of the shaped catalyst elements. It has been found that the pore volume of the catalysts useable in accordance with the invention must be in an optimal range to produce optimal results in the process of this invention for the hydrogenation of fatty acid methyl esters. In one preferred embodiment, metal-containing catalysts are used where the pore volume is in the range from 0.4 to 0.6 cm$^3$/g. A pore volume in this range also has the advantage of contributing to increasing the activity and selectivity of the hydrogenation catalysts. High activities and selectivities are obtained both in trickling bed reactors and in sump phase reactors. At the same time, the catalysts as described herein have an extremely long useful life in the process of this invention and do not present problems during the separation of catalyst and reaction products.

The catalysts used in the process of this invention are activated with hydrogen or with a hydrogen-containing gas mixture before they are used in the hydrogenation of fatty acid methyl esters. For reasons of economy, a gas mixture predominantly consisting of a nitrogen/hydrogen gas mixture is advantageously used for activation of the catalyst. As known from the prior art, such activation is advantaegously carried out by drying the catalyst masses in a stream of nitrogen at elevated temperature after their production and adding hydrogen in increasing quantities to the drying gas for activation. The proportion of hydrogen in the activating gas mixture is maintained between 0.1 and 10% by volume. The activation of the catalysts is carried out both in situ and optionally in a vessel separate from the reaction vessel.

The reaction temperatures in the hydrogenation of fatty acid methyl esters in accordance with the process of the present invention are maintained in the range from 160° to 270° C. and, preferably, in the range from 180° to 240° C. In the temperature control of the reaction, a general factor to be taken into consideration is that the hydrogenation of the fatty acid methyl esters to fatty alcohols is an exothermic chemical reaction. Accordingly, in the control of the reaction temperature, it is important to ensure that, after the reduction of the fatty acid methyl esters has started, the heat of reaction is dissipated in an appropriate manner.

The process of this invention for the catalytic hydrogenation of fatty acid methyl esters is carried out under reaction pressures in the range from 20 to 100 bar. The preferred range for the reaction pressures is from 20 to 50 bar. These relatively low reaction pressures provide for high activity and selectivity of the catalysts, so that the volume/time yield of the process according to the invention lies in an optimal range.

The process of this invention for the hydrogenation of fatty acid methyl esters is also characterized in that a molar ratio of hydrogen to fatty acid methyl ester substrate is adjusted to a value of from 10:1 to 500:1.

A major advantage of the process of this invention lies in the ability to produce fatty alcohols from fatty acid methyl esters at reduced reaction pressures with high selectivity and low hydrocarbon formation employing improved copper chromite catalysts described herein.

The invention is illustrated by the following examples.

EXAMPLES

Production Example

Production of a catalyst 84.93 g Ba(NO$_3$)$_2$, 3493 g Cu(NO$_3$)$_2$ .2 H$_2$O, 294.43 g Mn(NO$_3$)$_2$ .4 H$_2$O and 62.3 g SiO$_2$ in the form of a 40% by weight silica sol were dissolved with vigorous stirring in 9 liters deionized water at temperatures of from 30° to 90° C. In a second vessel, 1639 g CrO$_3$ were dissolved in 9 liters deionized water under the same conditions, followed by the addition of 3650 g of a 25% ammonia solution. The solution containing barium, manganese and copper was then pumped at 30° to 90° C. into the ammonium chromate solution, a mixture of barium chromate, manganese hydroxide, silicon hydroxide and copper chromate being precipitated from the solution. Precipitation stopped when the pH value fell below 7.

The precipitate was filtered in a frame filter press and washed with deionized water until free from nitrate. The filter cake was dried overnight at 90° to 120° C. and then reduced to a coarse powder in a cutting mill. The resulting chromate powder was thermally decomposed ("calcined") to chromite at 300° to 500° C. in a revolving tube furnace. The calcined powder-form material had the following chemical composition:

| | |
|---|---|
| Cu: | 38 ± 0.5% |
| Cr: | 29 ± 0.5% |
| Mn: | 2.5 ± 0.5% |
| Ba: | 1.9 ± 0.5% and |
| Si: | 1 ± 0.3% |

5% by weight graphite was added to 1 liter of the powder, followed by mixing for 15 minutes in a Loedige mixer. 10% by weight of a 40% by weight polyvinyl acetate suspension were then added, followed by brief mixing until agglomerates began to build up. The powder was then compacted to small granulates in a perforated-roll granulator, dried to a residual moisture content of 10 to 15% and sieved to a 0.6 to 2 mm grain fraction.

The granulate had excellent flow properties and could be compressed in a rotary tabletting machine to tablets 3 to 6 mm in diameter and 2 to 4 mm thick.

After hardening of the tablets (6h, 200° C., in air), the specific BET surface measured 40±10 m$^2$/g for a pore volume of from 0.4 to 0.6 cm$^3$/g.

EXAMPLES 1 to 5

Comparison Example 1

A mixture of fatty acid methyl esters having chain lengths of from 12 to 18 carbon atoms was continuously reacted in co-current with hydrogen in a 1 liter trickling-bed reactor which had been charged with catalyst tablets (diameter 4 mm, height 4 mm) according to the Production Example.

The liquid and condensable reaction products were collected by two-stage separation in pressure vessels.

The process parameters and the results obtained are shown in the following Table.

| Examples: | 1 | 2 | 3 | 4 | 5 | Comp. 1 |
|---|---|---|---|---|---|---|
| Reaction pressure (bar) | 50 | 50 | 30 | 30 | 20 | 10 |
| Reaction temperature (°C.) | 200 | 205 | 200 | 250 | 200 | 250 |
| LHSV* ($1 \times 1^{-1} \times h^{-1}$) | 1.0 | 1.0 | 0.5 | 1.0 | 0.5 | 0.5 |
| $H_2$: substrate (mol $\times$ mol$^{-1}$) | 100 | 200 | 100 | 200 | 100 | 100 |
| Saponification value of product | 4.5 | 2.8 | 0.8 | 0.7 | 2.5 | 3.1 |
| Composition of product (% by weight): | | | | | | |
| Fatty alcohols | 84.3 | 84.9 | 85.6 | 83.3 | 84.8 | 79.4 |
| Hydrocarbons | 0.06 | 0.07 | 0.12 | 2.36 | 0.25 | 5.5 |
| Methanol | 13.7 | 13.8 | 14.0 | 13.9 | 13.8 | 13.8 |

LHSV* (liquid hourly space velocity)

What is claimed is:

1. A process for the catalytic hydrogenation of fatty acid methyl ester mixtures which comprises the steps of:
   A. continuously reacting fatty acid methyl esters with hydrogen at a pressure of from about 20 to about 100 bar and a temperature of from about 160° to about 270° C. at a molar ratio of hydrogen to fatty acid methyl ester of from about 10:1 to about 500:1 in the presence of a particulate and/or granulated calcined oxidic catalyst activated by hydrogen or hydrogen containing gas and prepared from a mixture containing from about 30 to about 40% by weight copper, from about 23 to about 30% by manganese, from about 1 to about 10% by weight silicon, weight chromium, from about 1 to about 10% by weight silicon, from about 1 to about 7% by weight barium, from about 1 to about 10% by weight of at least one binder and from about 1 to about 10% by weight graphite, the percentages by weight being based on the total weight of the oxidic catalyst to form a reaction product containing a mixture of fatty alcohols and methanol, and
   B. Separating the reaction product from the catalyst.

2. The process of claim 1 wherein said catalyst contains from about 32 to about 38% by weight copper.

3. The process of claim 1 wherein said catalyst contains from about 26 to abut 29% by weight chromium.

4. The process of claim 1 wherein said catalyst contains from about 1.5 to about 3% by weight barium.

5. The process of claim 1 wherein said catalyst contains from about 1.5 to about 3% by weight silicon.

6. The process of claim 1 wherein said catalyst contains from about 32 to about 38% by weight copper, from about 26 to about 29% by weight chromium, from about 1 to about 6% by weight manganese, from about 1.5 to about 3% by weight barium, and from about 1.5 to about 3% by weight silicon.

7. The process of claim 1 wherein said catalyst contains from about 32 to about 38% by weight copper, from about 26 to about 29% by weight chromium, from about 1 to about 6% by weight manganese, from about 1.5 to about 3% by weight barium, from about 1.5 to about 3% by weight silicon and from about 1 to about 5% by weight of at least one of zirconium and cerium.

8. The process of claim 7 wherein said catalyst contains from about 2 to about 3% by weight of at least one of said zirconium and cerium.

9. The process of claim 1 wherein said binder is selected from polyvinyl acetate and methyl methacrylate.

10. The process of claim 1 wherein said catalyst has a grain size of from about 0.6 to about 3.0 mm.

11. The process of claim 1 wherein said particulate and/or granulated catalyst has a diameter of from about 1 to about 6 mm and a length of from about 1 to about 6 mm.

12. The process of claim 1 wherein said catalyst has a specific surface of from about 30 to about 50 m$^2$/g.

13. The process of claim 1 wherein said catalyst has a pore volume of from about 0.4 to about 0.6 cm$^3$/g.

14. The process of claim 1 wherein said catalyst is activated with an N$_2$H$_2$ gas mixture containing from about 0.1 to about 10% by volume hydrogen.

15. The process of claim 1 wherein the reaction pressure is maintained between bout 20 to about 50 bar.

16. The process of claim 1 wherein the reaction temperature is maintained between about 180° to about 240° C.

17. The process of claim 1 wherein said catalytic hydrogenation is carried out in a trickling bed reactor.

* * * * *

UNITED STATES PATENT AND TRADEMARK OFFICE
CERTIFICATE OF CORRECTION

PATENT NO. : 5,124,491
DATED : June 23, 1992
INVENTOR(S) : Fleckenstein, et. al.

It is certified that error appears in the above-indentified patent and that said Letters Patent is hereby corrected as shown below:

```
Column 7, line 33, claim 1, "manganese" should read --weight chromium --.
Column 7, line 33, claim 1, "after "chromium" insert --from about t to about
10% by weight manganese --.
Column 7, line 34, claim 1, Omit "weight chromium".
```

Signed and Sealed this

Twenty-eighth Day of June, 1994

Attest:

BRUCE LEHMAN

*Attesting Officer*    Commissioner of Patents and Trademarks